United States Patent [19]

Quadro

[11] 4,358,444

[45] Nov. 9, 1982

[54] 2,4-DIOXACYCLOHEXANONE DERIVATIVE

[75] Inventor: Giuseppe Quadro, Milan, Italy

[73] Assignee: Dr. L. Zambeletti S.p.A., Baranzate, Italy

[21] Appl. No.: 306,183

[22] Filed: Sep. 28, 1981

[30] Foreign Application Priority Data

May 7, 1981 [IT] Italy ................... 21558 A/81

[51] Int. Cl.³ ............... A61K 31/60; A61K 31/625; C07D 319/08
[52] U.S. Cl. ................... 424/230; 549/274; 424/232
[58] Field of Search ........... 260/340.2; 424/230, 424/232; 549/274

[56] References Cited

U.S. PATENT DOCUMENTS 3,420,830  1/1969  Fried ........................ 544/93

4,046,887  9/1977  Paris et al. ................. 260/340.2

Primary Examiner—Norma S. Milestone
Attorney, Agent, or Firm—Bucknam and Archer

[57] ABSTRACT

3-(2-Methoxy-phenoxy)-3-methyl-benzo-2,4-dioxacyclohexanone of formula

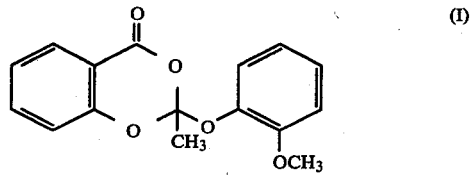

a process for its preparation through reaction among the chloride of acetylsalicylic acid, guaiacole and pyridine; pharmaceutical compositions containing it.

2 Claims, 1 Drawing Figure

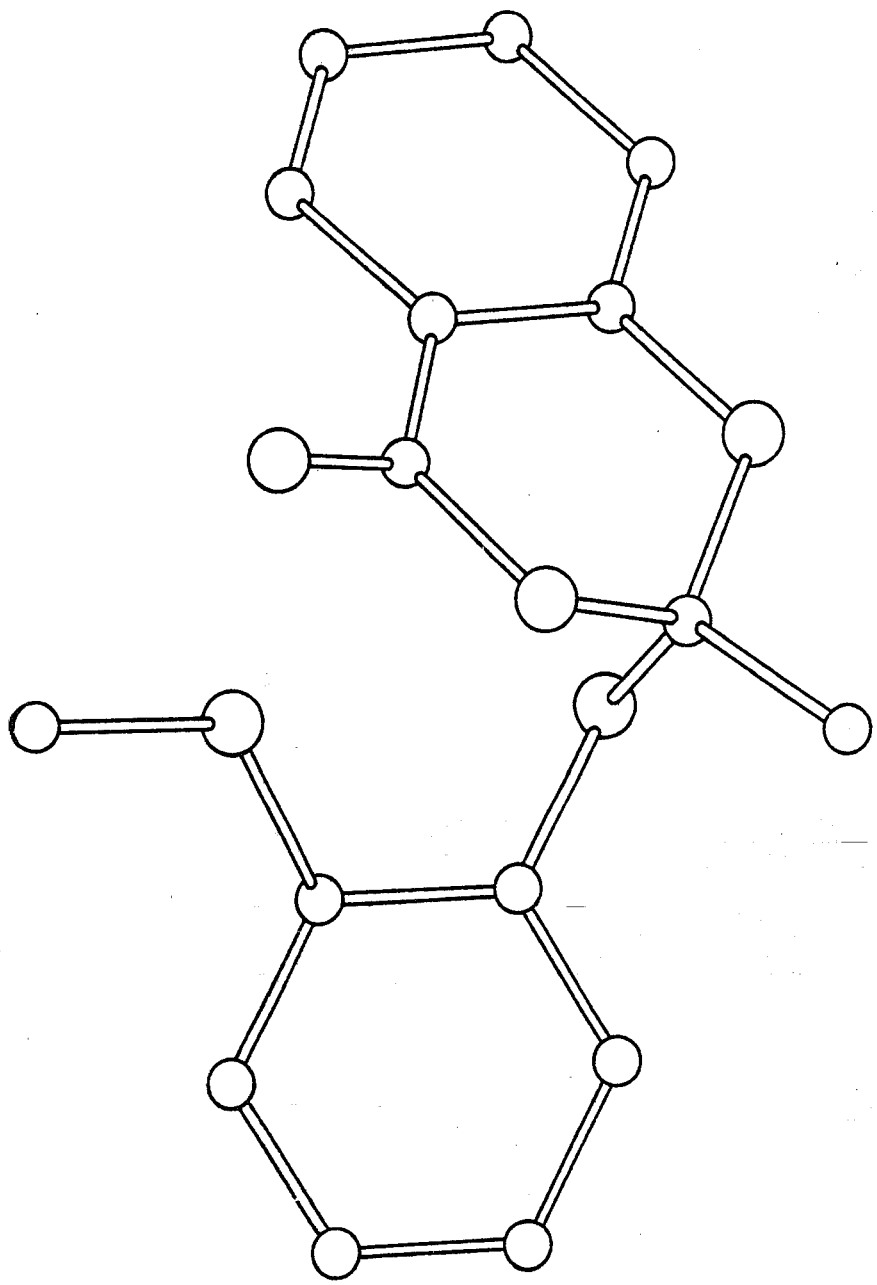

2,4-DIOXACYCLOHEXANONE DERIVATIVE

DESCRIPTION OF THE INVENTION

The presente invention refers to 3-(2-methoxyphenoxy)-3-methyl-benzo-2,4-dioxacyclohexanone of formula

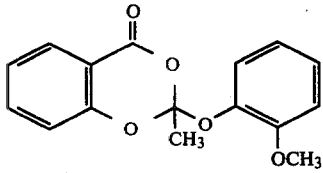

(I)

This compound displays remarkable pharmacological properties. As an example, it is endowed with an antitussive activity higher than that of codeine, an antiinflammatory action which practically is the same as that possessed by acetylsalicylic acid and an antipyretic activity which is only slightly lower than that displayed, again, by acetylsalicylic acid. These favorable biological properties, coupled with a complete absence of any gastrolesive effect and an almost negligible toxicity (both acute, subacute and chronic) cause this substance to be perfectly tolerable at gastric level and, accordingly, particularly suitable for oral and rectal administration.

The compound of the invention, hereinafter referred to as MR 693 for brevity purposes, is prepared by reacting the chloride of acetylsalicylic acid, guaiacol and pyridine in the molar ratio 1:1:1. The reaction is carried out in inert organic solvents such as, for instance, methylene chloride.

The following non-limitative example is provided only with the purpose of better illustrating the invention.

EXAMPLE (a) The chloride of acetylsalicylic acid was prepared by boiling for 3 hours the acid and thionyl chloride, evaporating off the excess of thionyl chloride and distilling the obtained residue under vacuum (150° C./30 mm Hg).

Yield: 50–70% of theoretical.

The obtained chloride was kept at 0°–4° C. for 18 hours.

(b) A solution of 709 g (3.57 mole) of the chloride of acetylsalicylic acid obtained as under (a) in 685 ml of methylene chloride was added with 442 g (3.57 mole) of guaiacol. The resulting mixture was externally cooled by a water bath, then 282 g (3.57 mole) of pyridine were added dropwise, keeping the reaction temperature at 20°–25° C. After the addition was completed, the stirring was prolonged for about one further hour, then the mixture was left standing for 16 hours.

The mixture was washed several times with water, the organic phase was dried over anhydrous sodium sulfate and finally evaporated under reduced pressure. The obtained yellow residue crystallized slowly. It was taken up after 48 hours with a small amount of ethanol, the resulting mixture was filtered and the obtained crystals were washed. After crystallization from ethanol 291 g of the compound of formula I, melting at 70°–74° C., were obtained.

The elemental analysis is in accordance with the proposed structure, which has also been confirmed by crystallographic investigations:

MR 693 (empirical formula $C_{16}H_{14}O_5$; m.w.=286.29)

Crystallizes in the orthorombic system, spacial group Pbca.

The cell parameters are: a=9.968(3), b=23.808(4), c=11.668(2) Å; V=2769(2) Å. They have been determined through a square-minimums analysis of the $\sin^2 \theta$ values of 50 reflexes. The measures have been carried out by an authomatic diffractometer CAD4 (Nonius), by utilizing the Mo K$\alpha$ radiation ($\alpha$=0.71069 Å), with graphite monochromator. The density, calculated for 8 molecules in the cell, is 1.373 g/cm; the experimental value (by flotation in $K_2HgI_4$ solution) is 1.370 g/cm.

On an approximatively spherical crystal (diameter of around 0.28 mm), using the same diffractometer and employing the omega-scan technique at variable speed, 2377 intensities have been measured. The periodical control of three standard intensities has shown no deterioration of the crystal. The data have been corrected by the Lorentz- and polarization factors; no absorption correction has been necessary [$\mu$(Mo K$\alpha$)=1.1 cm$^{-1}$].

The structure (see the attached drawing) has been resolved by the direct methods. The final refining of 247 parameters (scale factor, secondary extinction coefficient, cohordinates and thermal anisotropic factors for 16C and 5O, cohordinates and isotropic B factors for 14H) has been performed through subsequent cycles of complete matrix square minimums, based on 2055 reflexes with positive intensity. The minimized amount has been $$\Sigma w(F_o - F_c)^2, \text{ with weights } w = 4F_o^2/\sigma^2(F_o)^2.$$

The final variance index $R = (\Sigma ||F_o| - |F_c||/\Sigma |F_o|)$ is 0.069, calculated on the 2055 reflexes utilized in the refining; the weight index $R_w$ is 0.036 [for the 1662 reflexes with $F^2 > \sigma(F^2)$ the values of R and Rw are 0.048 and 0.035 respectively].

The pharmacological and toxicological properties of MR 693 are outlined below.

PHARMACOKYNETIC AND METHABOLISM

Studies have been performed both in vitro and in vivo. The in vitro experiments have shown that compound MR 693 is enzymatically hydrolyzed to acetylsalicilic acid and guaiacol. The organs displaying the highest esterase activity proved to be the lungs and the kidneys. As MR 693 does not possess any ionizable functional group, it is highly lipophylic and one can reasonably assume that it passes very easily through the intestinal epithelium.

The in vivo experiments have confirmed that the compound according to the invention, which is absorbed as such for the major part after oral administration, is hydrolyzed to acetylsalicylic acid, salycilic acid and guaiacol. The salycilic acid and its acetylderivative enter the systemic circulation and are excreted by urinary route.

On the contrary, the guaiacole is mainly absorbed by pre-systemic route; it enters the lungs through the lymphatic vessels and is eliminated by respiratory route.

The concentrations of salycilic acid and acetylsalycilic acid observed in the lungs after administration of MR 693, have proven to be higher than those observed in the plasma and the liver. It may therefore be assumed that the marked pulmonary tropism of guaiacol also implies a relative better pulmonary tropism for the compound MR 693.

ANTITUSSIVE ACTIVITY

The experiments have been carried out on guinea pigs by using the citric acid aerosol induced cough method. The efficacy of MR 693 has been investigated by administering the compound by oral and intraperitoneal route and using codeine as the comparison compound i.e., a well known and widely employed antitussive agent.

From the obtained results, which are summarized in the following Table 1, it can be inferred the following:

oral administration

At the tested dose of 500 mg/kg, MR 693 causes a marked reduction over the controls of the number of cough-strokes. Said activity is better than that displayed, under the same conditions, by an oral dosage of 25 mg/kg of codeine.

intraperitoneal administration

MR 693 displays an excellent activity also when administered by this route. At a dosage of 100 mg/kg a 100% reduction over the controls of the number of cough-strokes has been observed, whereas codeine at 12.5 mg/kg, again administered by intraperitoneal route, has caused a reduction of 93%.

TABLE 1

Citric acid aerosol induced cough test in guinea pigs: antitussive activity of MR 693 and codeine

| Compound | Dose (mg/kg) | Administration route | % Inhibition of cough-strokes |
|---|---|---|---|
| MR 693 | 500 | os | 84.3 |
|  | 100 | i.p. | 100.0 |
| Codeine | 25 | os | 76.7 |
|  | 12.5 | i.p. | 93.7 |

GASTROLESIVE ACTIVITY

MR 693 and acetylsalycilic acid as the comparison substance were administered by oral route to rats fastened from at least 18 hours.

After six hours from the beginning of the experiment, the rats were sacrificed and the stomachs were opened and examined in order to verify the presence of lesions on the gastric mucosa.

The obtained results, expressed as average diameter (in mm) of the lesions, are reported in the following Table 2: they clearly show that the compound according to the present invention, unlike acetylsalycilic acid, is perfectly tolerated at gastric level.

TABLE 2

Gastrolesive activity in rats of MR 693 and acetyl-salycilic acid after oral administration

| Compound | Dose (mg/kg os) | Average diameter of the lesions (mm) |
|---|---|---|
| Controls | — | 0.1 ± 0.1 |
| MR 693 | 100 | 0 |
|  | 400* | 0 |
| Acetylsalycilic acid | 250* | 3.7 ± 0.8 |

*Equimolecular dosages.

ANTINFLAMMATORY ACTIVITY

The antinflammatory properties of MR 693 have been investigated by means of the carrageenin induced edema test in rats, by administering the compound of the invention by oral route and using acetylsalycilic acid as the comparison substance, at equimolecular dosages.

The obtained results clearly show that MR 693 causes a marked reduction of the edema and that this reduction is practically of the same level as that displayed by the comparison substance. These results are summarized in the following Table 3.

TABLE 3

Carrageenin induced edema test in rats: antinflammatory activity of equimolecular dosages of MR 693 and acetyl-salycilic acid

| Compound | Dose (mg/kg os) | % Inhibition of the edema |
|---|---|---|
| MR 693 | 400 | 30 |
| Acetylsalycilic acid | 250 | 33 |

ANTIPYRETIC ACTIVITY

This activity has been investigated by means of the yeast induced hypertermia test in the rat, taking again acetylsalycilic acid, administered at equimolecular dosages, as the comparison substance.

The obtained results, which are summarized in the following Table 4 show that MR 693 possesses a marked antipyretic activity, which is only slightly lower than that displayed by acetylsalycilic acid.

TABLE 4

Yeast induced hypertermia test in rats: antipyretic activity of equimolecular dosages of MR 693 and ace-tylsalycilic acid

| Compound | Dose (mg/kg os) | % Inhibition |
|---|---|---|
| MR 693 | 400 | 86 |
| Acetylsalycilic acid | 250 | 103 |

TOXICITY

Acute toxicity

Acute toxicity tests have been carried out in mice rats, by administering the compound of the invention by oral and intraperitoneal route. As it can be seen from the results reported in the following Table 5, mr 693 can be considered as a very little toxic compound.

TABLE 5

Acute toxicity of MR 693 in mice and rats

| Animal specie | Administration route | $DL_{50}$ mg/kg |
|---|---|---|
| Mouse | os | >3000 |
| Rat | os | >3000 |
|  | i.p. | 1750 |

SUBACUTE TOXICITY

Subacute toxicity studies have been carried out on rats and dogs, by administering MR 693 by oral route for four consecutive weeks.

The parameters which have been taken into consideration are as follows:
behavior
mortality
weight increase
haematological data
haematochemical data
glycosuria, proteinuria, albuminuria and haematuria
autoptic examination
weight of the principal organs hystological investigation of the principal organs; but in no case alterations or malformations ascribable to the treatment with the compound of the invention have ever been evidenced.

CHRONIC TOXICITY

Chronic toxicity studies have been carried out on rats, administered by oral route with MR 693 for 24 consecutive weeks, and dogs, administered by oral and rectal route with the compound of the invention again for 24 weeks.

The parameters which have been taken into consideration are as follows:
general conditions
behavior
mortality
haematic crasis
biochemical examination of the blood glycosuria, proteinuria, haematuria, albuminuria
autoptic examination
weight and hystological control of the principal organs;
but no alterations or particularly significant anatomo-pathological states have ever been evidenced.

Besides, the investigation of the gastro-intestinal tract did not show any alteration of the mucosae.

THERATOGENESIS

Theratogenesis studies have been carried out on rats and rabbits, which have been treated by oral route with MR 693 all along the duration of the pregnancy.
The investigation of:
number of pregnant females
number of dead females
initial body weight/end body weight (of the mothers)
total number of foetuses
average number of lived foetuses
total number of dead foetuses
total number of re-absorptions
average weight of lived foetuses
possible malformations
has shown that the treatment with MR 693 has caused no alteration. As a matter of fact, neither somatic not skeletal malformations have been observed, as well as no variation of the number of litters alive.

PHARMACEUTICAL COMPOSITIONS

The compound according to the invention may be administered by oral or rectal route, and is embodied in various pharmaceutical compositions such as, for instance:
tablets and capsules containing 0.5 g of the active ingredient
5.0% and 3.3% (by weight) suspensions suppositories containing 1.2 and 0.5 of the active ingredient.

I claim:
1. 3-(2-Methoxy-phenoxy)-3-methyl-benzo-2,4-dioxacyclohexanone of formula

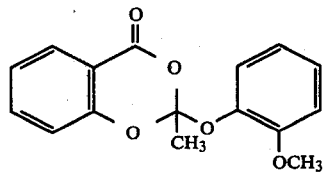

2. Pharmaceutical compositions having antitussive, antipyretic and antiinflammatory activities, suitable for oral or rectal administration containing, as the active ingredient, an antitussive, antipyretic and antiinflammatory effective amount of the compound as defined in claim 1.

* * * * *